(12) United States Patent
Karakotsios et al.

(10) Patent No.: US 8,942,434 B1
(45) Date of Patent: Jan. 27, 2015

(54) CONFLICT RESOLUTION FOR PUPIL DETECTION

(75) Inventors: Kenneth M. Karakotsios, San Jose, CA (US); Isaac S. Noble, Soquel, CA (US); Edwin Joseph Selker, Palo Alto, CA (US)

(73) Assignee: Amazon Technologies, Inc., Reno, NV (US)

( * ) Notice: Subject to any disclaimer, the term of this patent is extended or adjusted under 35 U.S.C. 154(b) by 407 days.

(21) Appl. No.: 13/332,128

(22) Filed: Dec. 20, 2011

(51) Int. Cl.
*G06K 9/00* (2006.01)
*A61B 3/14* (2006.01)

(52) U.S. Cl.
CPC ............ *G06K 9/00597* (2013.01); *A61B 3/14* (2013.01)
USPC ........... 382/117; 382/103; 382/305; 351/206; 345/619

(58) Field of Classification Search
CPC .... G06T 7/004; A61B 3/113; G06K 9/00597; G06K 9/00604; G06K 9/00228; G06K 9/00261; G06K 9/00248
USPC ......... 382/103, 115, 117, 168–172, 190, 195, 382/244, 305; 345/418–420, 619; 348/207.99, 222.1; 351/204–210, 221; 600/301; 606/5
See application file for complete search history.

(56) References Cited

U.S. PATENT DOCUMENTS

| | | | |
|---|---|---|---|
| 5,850,211 A | 12/1998 | Tognazzini | |
| 6,959,102 B2 | 10/2005 | Peck | |
| 7,092,554 B2 * | 8/2006 | Chen et al. | 382/118 |
| 7,199,767 B2 | 4/2007 | Spero | |
| 8,064,647 B2 * | 11/2011 | Bazakos et al. | 382/117 |
| 8,644,565 B2 * | 2/2014 | Du et al. | 382/118 |
| 2002/0180799 A1 | 12/2002 | Peck et al. | |
| 2003/0142068 A1 | 7/2003 | DeLuca et al. | |
| 2004/0174496 A1 * | 9/2004 | Ji et al. | 351/209 |
| 2004/0190759 A1 * | 9/2004 | Caldwell | 382/117 |
| 2005/0133693 A1 | 6/2005 | Fouquet et al. | |
| 2005/0175218 A1 * | 8/2005 | Vertegaal et al. | 382/103 |
| 2005/0207614 A1 * | 9/2005 | Schonberg et al. | 382/100 |
| 2005/0248529 A1 | 11/2005 | Endoh | |
| 2006/0077347 A1 * | 4/2006 | Liang et al. | 351/221 |
| 2006/0109422 A1 * | 5/2006 | Clark et al. | 351/205 |
| 2006/0147094 A1 * | 7/2006 | Yoo | 382/117 |

(Continued)

OTHER PUBLICATIONS

"Faceshift Documentation: Faceshift Studio Beta", http://www.faceshift.com/help/studio/beta/, 2012, 12 pages.
"Final Office Action dated Oct. 23, 2013", U.S. Appl. No. 12/786,297, 15 pages.
"Final Office Action dated Jun. 3, 2013", U.S. Appl. No. 13/083,303, 17 pages.

(Continued)

*Primary Examiner* — Chan Park
*Assistant Examiner* — Mia M Thomas
(74) *Attorney, Agent, or Firm* — Novak Druce Connolly Bove + Quigg LLP

(57) ABSTRACT

The pupil locations of a user with respect to a computing device can be determined by capturing one or more images of the user and analyzing those images using a set of pupil detection algorithms. Each algorithm can produce at least one estimated position with an associated confidence value, and this information from each algorithm can be used to determine a probable location of each pupil. In some embodiments, one or more environmental factors can be used to adjust the confidence values or select algorithms based on how the corresponding algorithms perform under those conditions. Similarly, an independence of the various algorithms can be utilized in some embodiments to adjust the confidence levels or weight results based on a level of dependence between those algorithms.

23 Claims, 9 Drawing Sheets

(56) References Cited

U.S. PATENT DOCUMENTS

| | | | |
|---|---|---|---|
| 2006/0256133 A1* | 11/2006 | Rosenberg | 345/619 |
| 2006/0257026 A1* | 11/2006 | Shiffer et al. | 382/190 |
| 2006/0269105 A1* | 11/2006 | Langlinais | 382/105 |
| 2007/0025598 A1* | 2/2007 | Kobayashi et al. | 382/117 |
| 2007/0189582 A1* | 8/2007 | Hamza et al. | 382/117 |
| 2008/0122803 A1 | 5/2008 | Izadi et al. | |
| 2008/0170759 A1* | 7/2008 | Monro | 382/117 |
| 2008/0253622 A1* | 10/2008 | Tosa et al. | 382/117 |
| 2009/0115966 A1* | 5/2009 | Waldorf et al. | 351/210 |
| 2009/0196460 A1 | 8/2009 | Jakobs et al. | |
| 2010/0002912 A1* | 1/2010 | Solinsky | 382/117 |
| 2010/0014718 A1* | 1/2010 | Savvides et al. | 382/117 |
| 2010/0014720 A1* | 1/2010 | Hoyos et al. | 382/118 |
| 2010/0066676 A1 | 3/2010 | Kramer et al. | |
| 2010/0097332 A1 | 4/2010 | Arthur et al. | |
| 2010/0125816 A1 | 5/2010 | Bezos | |
| 2011/0006978 A1 | 1/2011 | Yuan | |
| 2011/0026014 A1* | 2/2011 | Mack et al. | 356/124 |
| 2011/0128223 A1 | 6/2011 | Lashina et al. | |
| 2011/0128365 A1* | 6/2011 | Ren et al. | 348/78 |
| 2011/0141436 A1* | 6/2011 | Ono | 351/206 |
| 2012/0206333 A1 | 8/2012 | Kim | |
| 2013/0293530 A1* | 11/2013 | Perez et al. | 345/418 |

OTHER PUBLICATIONS

"International Preliminary Examination Report on Patentability dated Oct. 17, 2013", International Application PCT/US2012/032148, 5 pages.

"International Search Report dated Jul. 26, 2012", International Application PCT/US2012/032148, 7 pages.

"Non Final Office Action dated Nov. 7, 2013", U.S. Appl. No. 13/246,561, 18 pages.

"Non Final Office Action dated Dec. 6, 2012", U.S. Appl. No. 13/083,303, 16 pages.

"Non Final Office Action dated Mar. 28, 2013", U.S. Appl. No. 12/786,297, 15 pages.

"Notice of Allowance dated Aug. 14, 2013", U.S. Appl. No. 13/083,303, 6 pages.

Cappelletta, Luca et al., "Phoneme-To-Viseme Mapping for Visual Speech Recognition", Department of Electronic and Electrical Engineering, Trinity College Dublin, Ireland, 2012, 8 pages.

Cornell, Jay, "Does This Headline Know You're Reading It?", h+ Magazine, located at <http://hplusmagazine.com/articles/ai/does-headline-know-you%E2%80%99re-reading-it>, last accessed on Jun. 7, 2010, Mar. 19, 2010, 4 pages.

Van Den Berg, Thomas T., "Near Infrared Light Absorption in the Human Eye Media", Vision Res., vol. 37, No. 2, 1997, pp. 249-253.

* cited by examiner

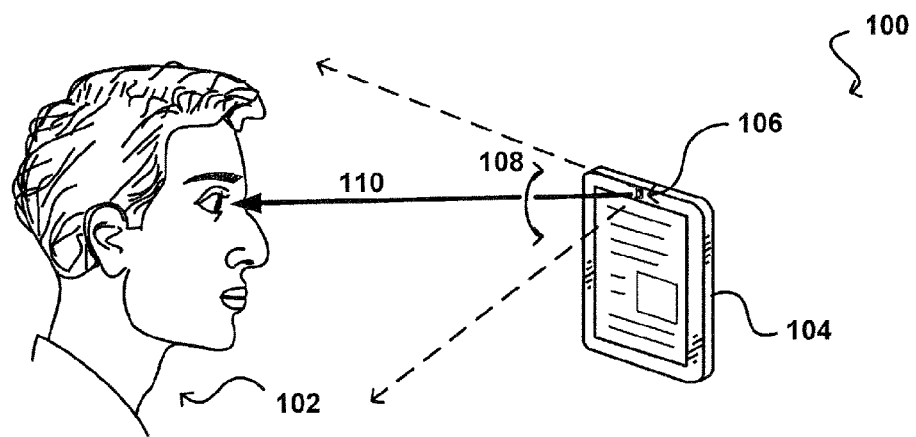
FIG. 1
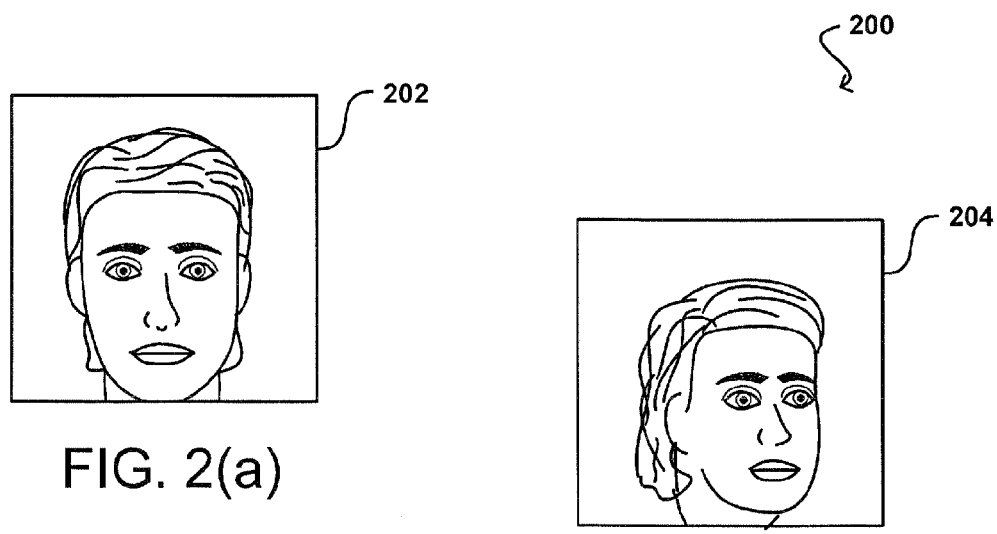
FIG. 2(a)
FIG. 2(b)
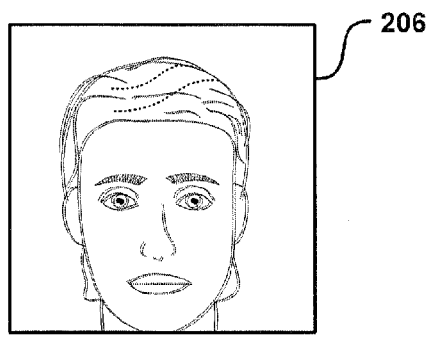
FIG. 2(c)

CONFLICT RESOLUTION FOR PUPIL DETECTION

BACKGROUND

People are utilizing electronic devices for an increasing variety of tasks. With the increase in utilization comes an interest in improving the ways in which users interact with these devices. One approach to enabling a user to provide input to an electronic device involves monitoring a gaze direction with respect to a user device, such that the user can provide input based on where the user is looking. Conventional approaches for determining where a user is looking involve tracking motion of the user's eyes over time. This typically involves an expensive set of electronics positioned in a stationary way in order to provide an acceptable level of accuracy. These approaches, however, are generally not accurate enough to provide for fine control of an element such as a cursor of an interface, particularly for a relatively small portable device with a relatively small display screen. The approaches also tend to be more expensive than is practical for many consumer devices. Further still, small portable devices can be held in a user's hand and thus can be subject to small movements that can negatively impact the accuracy of these approaches.

BRIEF DESCRIPTION OF THE DRAWINGS

Various embodiments in accordance with the present disclosure will be described with reference to the drawings, in which:

FIG. 1 illustrates an environment in which an electronic device is able to attempt to determine a gaze direction of a user in accordance with various embodiments;

FIGS. 2(a), (b), and (c) illustrate example images of a user captured under different conditions that can be analyzed in accordance with various embodiments;

DETAILED DESCRIPTION

Figure 3A:
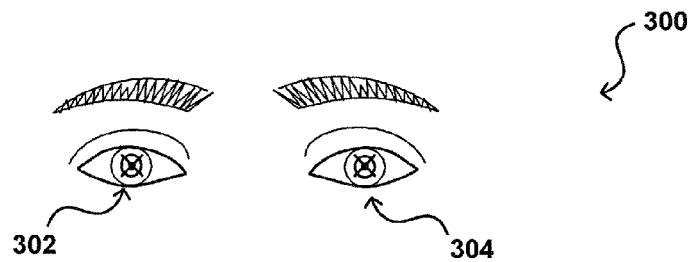
FIGS. 3(a), (b), (c), (d), (e), (f), and (g) illustrate an example approaches to determining pupil location that can be utilized in accordance with various embodiments.

Systems and methods in accordance with various embodiments of the present disclosure may overcome one or more of the aforementioned and other deficiencies experienced in conventional approaches to determining a relative position of the eyes of a user with respect to a computing device. In particular, various embodiments utilize a set of pupil or eye location determination algorithms to attempt to determine a probable relative position of the pupils of a user with respect to a computing device. The device can capture image information including at least a portion of a user, and the image information can be analyzed by the set of algorithms. Each algorithm can produce a set of results, such as an estimated location and a confidence value. The location and confidence values from the various algorithms can be combined to attempt to determine a probable location of the user's pupils, as may be useful for gaze tracking or other such processes.

In some embodiments, the agreement between location estimates can be weighed against the confidence values in each position estimate. Other factors can be included in the determination as well. For example, certain algorithms may perform poorly under certain environmental conditions, such as for images captured in bright light or of a user not directly facing the device. Accordingly, confidence values from different algorithms can be adjusted based at least in part upon the environmental conditions at the time of image capture and the performance of the set of algorithms used to analyze that image with respect to those conditions. Similarly, certain algorithms analyze similar types of information and are likely to produce similar results under various conditions. The relative independence among the set of algorithms can also be used to adjust the confidence values or weight the results for the location determination.

Various other applications, processes and uses are presented below with respect to the various embodiments.

FIG. 1 illustrates an example situation 100 wherein a user 102 is viewing content being displayed on an electronic device 104. In this example, the computing device has a camera 106 or other such imaging element operable to capture image information (e.g., still or video image information) within a field of view 108 of the camera. When a user is positioned within the field of view, the camera can capture one or more images (or segments of video) for at least a portion of the user, and can analyze the images to determine various types of information about the user. For example, the device might include algorithms for performing facial recognition to attempt to identify the user, gesture analysis to recognize one or more motions made by the user, or other such information. In at least some embodiments, the device 104 can attempt to determine information about the user's eyes, such as to determine a point of view of the user for content display or input, locate an iris for purposes of biometric identification, or determine a gaze direction of the user, which can be toward or away from the device, as an input or part of a gesture, etc. For many of these algorithms, the images are analyzed to attempt to locate one or more aspects of the user's eye, such as a location of at least one eye in the image, or a position of the pupils with respect to the position of the user's eyes for purposes of gaze determination. For example, the relative position of the user's eye in an image can be used with information about the camera used to capture that image (such as field of view, location of the camera relative to a device, and resolution of the camera) to determine a relative location or direction 110 of the user's eye with respect to the camera. Such information can be used to determine a point of view of the user, as may be important for interpreting gesture or motion information.

Similarly, the device can use the position of the user's pupils with respect to the location or point of view of the user to attempt to determine where the user is looking with respect to the device. For example, an algorithm can attempt to determine the location of the user's eyes with respect to the camera, as well as a relative location of each pupil with respect to the user's eyes. If the locations can be determined in three-dimensional space, such as by using stereo imaging or a distance determination element with a camera, then vector manipulation or another such approach can be used to determine where the user is looking with respect to the device. Examples of approaches to determining gaze direction and/or point of view can be found in co-pending U.S. patent application Ser. No. 13/083,303, filed Apr. 8, 2011, entitled "Gaze-Based Content Display," as well as co-pending U.S. patent application Ser. No. 13/246,561, filed Sep. 27, 2011, entitled "Point of View Determinations for Finger Tracking," each of which is hereby incorporated herein by reference.

As mentioned above, however, determining the relative positions of a user's pupils can be difficult, particularly for relatively inexpensive devices that can move over time. In many of these cases, the range of angles over which the user's eyes will move relative to a device such as a smart phone or portable media player is relatively small, such that small movements in gaze direction result in very small movements in pupil location in the captured image information. Further, the size of the user's pupils might not be very large in the captured images, such that the accuracy is limited by the relative size and number of the pixels of the camera sensor, as well as the resolving power of the sensor's lens. Further still, the device in many embodiments analyzes an image to attempt to determine which features in the image correspond to pupils, and not some other feature of a similar size, shape, color, or type. In many cases, the amount of lighting in the room, relative orientation of the user, movement of the camera, whether the user is wearing glasses, or other such environmental factors can impact the ability of an algorithm to identify a feature corresponding to a pupil, let alone accurately determine a center point or other position of the pupil.

For example, FIG. 2(a) illustrates an example image 202 of a set of images 200 illustrating a first situation where the user is facing the device capturing the image under normal lighting conditions. In such a situation, many algorithms can produce a relatively accurate determination of pupil location with relatively high confidence values. In the situation illustrated in the image 204 of FIG. 2(b), however, the user is not facing directly into the camera. Such a situation can affect the shape of the user's eyes in the image, as well as the relative separation and other such information. Accordingly, certain algorithms might produce estimates of pupil location that are less accurate than for other algorithms. Similarly, FIG. 2(c) illustrates an example image 206 for a situation where there is an undesirable amount of light, such as too much or too little light, which causes issues with the image such as graininess, low contrast, and other such aspects which can also make it difficult to identify and estimate the positions of various features in the image, which can cause various algorithms to provide less accurate determinations of pupil position.

As mentioned, there are a variety different ways to attempt to determine the relative positions of a user's pupils with respect to a camera, which can rely on various algorithms and processes. FIG. 3(a) illustrates an example 300 of pupil position determination in accordance with one embodiment. In this example, an image has been analyzed to attempt to locate the user's eyes in the image. The image can also be analyzed to attempt to determine the regions of the image that correspond to the user's pupils. For each of these regions, an algorithm can attempt to calculate or estimate the position of a center point 302, 304 or other such point for each of the user's pupils. In some embodiments, an algorithm can identify the location of a pixel in the captured image corresponding to each center point, and can use this information with the knowledge about the camera configuration to determine a relative position in space of each pupil.

Figure 3B:
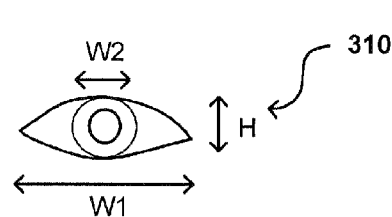

As mentioned, various approaches can be used to attempt to locate a user's pupils in one or more captured images. For example, FIG. 3(b) illustrates an example approach 310 wherein a shape-based approach can be used to attempt to identify a user's eye and pupil in an image. In this example, the algorithm can look to find shapes 310 that have specific dimension ratios. For example, the algorithm can attempt to identify elliptical shapes that have ranges of height and width. If a circle can be found within an ellipse that also has an appropriate range of dimension ratios (e.g., equal height and width measurements within 20% per unit length, for example) then that feature might be identified as a user's eye, iris, and/or pupil according to various algorithms. Shape-based algorithms can be affected by aspects such as device movement, blur, user orientation, and amount the user opens his or her eyes, among others.

Figure 3C:

FIG. 3(c) illustrates another example approach 320 wherein another shape-based algorithm can be used that attempts to locate circles 322 using another shape-based algorithm (or starburst algorithm, etc.) in accordance with various embodiments. In this example, the device can attempt to locate circular features of a certain size or dimension, concentric circles of various relative sizes, or other such information. In some embodiments, the algorithm can look at for concentric circles with relative color or intensity values, or other such information. As discussed above, such algorithms can be affected by aspects such as user orientation, movement, etc.

Figure 3D:
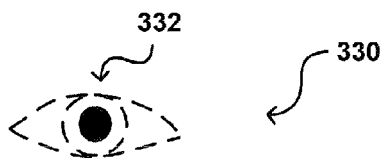

FIG. 3(d) illustrates another example approach 330 wherein an algorithm looks for retro-reflection in an image. In some embodiments, a computing device might flash an infrared (IR) LED or other such illumination device in order to illuminate the user with IR light. The retina of the human eye acts as a retro-reflector, and reflects the IR light back towards the device. A camera or sensor operable to capture IR light (or at least filter out other wavelengths to obtain an image containing substantially IR information) will then capture an image that can have strong reflections from the retina of the user, showing up as one or more discs 332 corresponding to the locations of the user's pupils. The reflection from other parts of the user can be less strong, such that the pupil location can appear very prominently in the image information captured under various environmental conditions. Once such a circle is located, a centroid calculation or other such determination can be used to determine a center point or other such location of the pupil or iris, which can assist with gaze determinations and other such aspects. Such algorithms can be affected by environmental aspects such as surrounding light sources and a user wearing glasses, for example.

In at least some embodiments, a retro-reflection approach will compare an image with active IR illumination against an image captured of the same area without active IR illumination. The area of strong difference is determined to correspond to the user's eyes. The level or amount of difference can indicate how directly the user is looking at the light source, which can assist with aspects such as gaze determinations. The absolute amount of light retro-reflected can vary significantly from person to person, however, and in some cases very little reflection may occur. In order to provide adequate results, particularly when a user is a substantial distance away, the IR illumination element would require a significant amount of power, which can make such an approach undesirable for at least certain applications.

Figure 3E:

FIG. 3(e) illustrates another example approach 340 wherein a shape algorithm looks for pairs of oriented triangular shapes 342 in an image, which can be indicative of the position of a user's eye. In some embodiments, this is used to locate the user's eyes in order to determine a field of search, whereby circles or other shapes can be located between the triangular features. Such an approach can be affected by environmental aspects such as those discussed above for other shape-based algorithms.

Figure 3F:
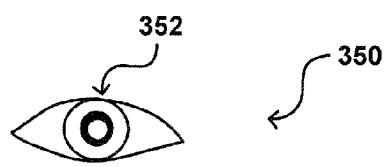

FIG. 3(f) illustrates another example approach 350, wherein an illumination source (such as a white light LED) on the computing device is activated in order to form a glint 352 on the user's cornea. In some embodiments, the reflection of a display screen or other such illumination source can be used to provide such a glint. An algorithm can look for glint locations in images, as may be determined based on shape and differences in intensity, in order to determine relative eye position. Such an approach can be affected by environmental conditions such as excess lighting or reflections, and in some cases the glint might affect the determination of pupil location.

Although not discussed in detail herein, there are also various other algorithms and approaches that can be used to determine relative pupil position or other such information. These can include, for example, various other shape, feature, model, intensity, or color-based algorithms as known in the art for use individually in locating and/or determining such information.

Figure 3G:
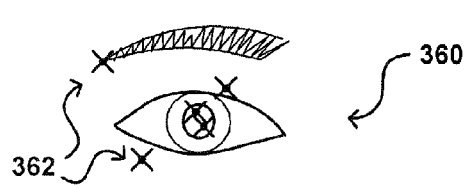

As can be seen, various environmental factors can affect different eye and pupil location algorithms in different ways. FIG. 3(g) illustrates an example of pupil location determinations 362 from different algorithms on the same image, captured for a given set of environmental conditions. As can be seen, the estimates of pupil location vary between the algorithms, and in some instances do not even correspond to the location of an eye, such as where an algorithm detected a corner of an eyebrow of the user. One approach would be to simply utilize two or more approaches and find a center point or average of the estimates. As illustrated in FIG. 3(g), however, the determination could vary by a large amount based upon which pair or group of measurements were taken.

Systems and methods in accordance with various embodiments utilize various combinations of algorithms to attempt to determine pupil locations and other such information. In order to correct for variations due to environmental conditions or other such factors, various embodiments also utilize one or more conflict resolution algorithms to attempt to select, determine, calculate, or estimate the best location based on the results of those algorithms. In at least some embodiments, each location determination algorithm can provide some indication of how accurate or confident the algorithm is in the produced result, and in some cases can provide more than one potential result for each pupil with a confidence level for each result. Based at least in part upon the determined confidence levels for each algorithm, various approaches can select position results that are more likely to provide accurate estimations of position. Such an approach can provide for improved pupil position determinations using less expensive components than conventional approaches, without a requirement for fixed positioning of the device. Further, such an approach enables accurate determinations for a variety of different environmental conditions or other such situations.

In at least some embodiments, each algorithm can provide a similar type of results, such as a pixel location, a vector, or an (x,y) coordinate of an image for each potential result, as well as a confidence level in each potential result. For example, an algorithm might provide the three results with the highest confidence values. In at least some embodiments, these position values and confidence levels can be combined using one or more statistical analysis approaches to attempt to determine a most probable location for each pupil. In other embodiments, a heat map can be generated to attempt to determine the most likely position. A heat map generally refers to a representation of data where the range of values is represented as a spectrum of colors. The most likely position might correspond to the "highest" point on the heat map, or the location where the value has the "highest" color value on the corresponding spectrum. In yet other approaches, a confidence value for each pixel can be provided as to the likelihood that the pixel corresponds to the pupil location. Various other approaches can be utilized as well as discussed and suggested elsewhere herein.

In a first approach, an algorithm might reject any position estimates that have a confidence level lower than a determined minimum confidence threshold, such as about 10%, 20%, or 30%. In some embodiments, the minimum confidence threshold might be different for different algorithms, as may be determined through a calibration or testing procedure, or using a feedback loop on a computing device, etc. The algorithm can then attempt to determine the likely position based on the determinations with more than the minimum confidence level. In some embodiments, any point with a confidence level above a certain threshold, such as above about 90%, might have that position information selected as the result to be used.

In some embodiments, an algorithm might utilize a combination of confidence level and agreement with other determinations to determine how much to weight a given result. For example, a first position determination with a confidence level of 30% (or 0.30 for a normalized confidence scale running from 0 to 1) might be given much less weight than a second position determination with a 60% confidence level. If, however, the first position determination is very close to a third position determination with a 50% confidence level, the algorithm might make a determination that the pupil position is likely near the first and third location determinations due at least in part to their proximity, instead of the second position determination which has a higher confidence value but is further away from the other two results. Various weightings and balances can be used in accordance with various embodiments.

Figure 4:
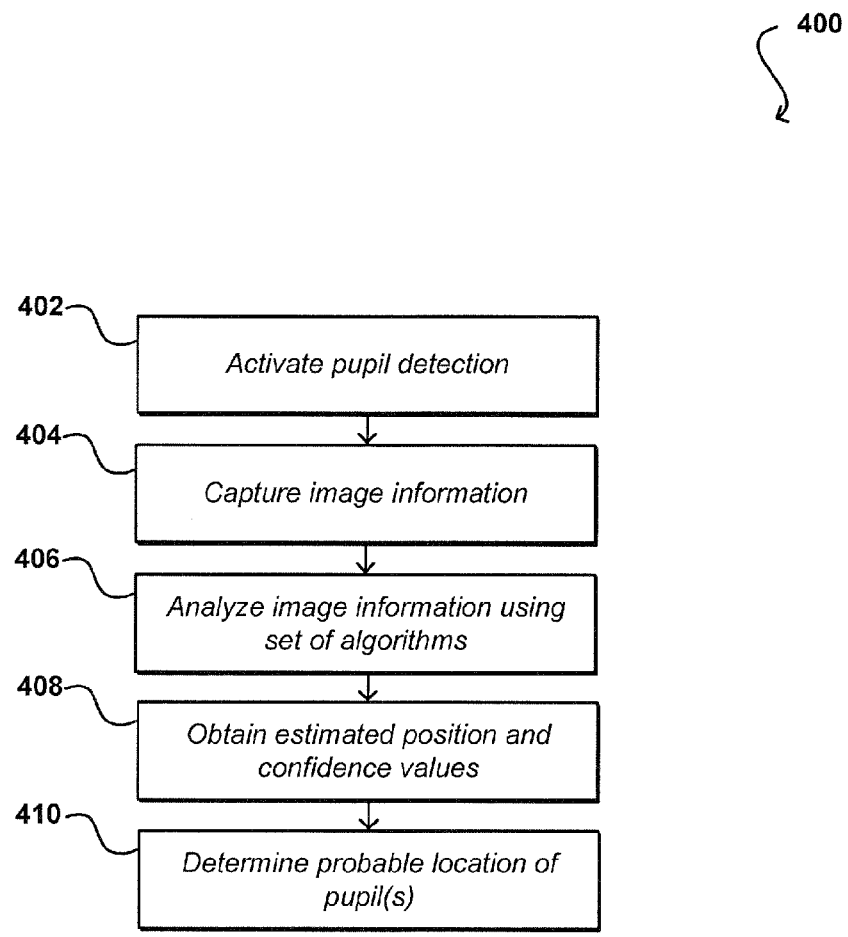
FIG. 4 illustrates an example process for determining pupil location that can be utilized in accordance with various embodiments.

FIG. 4 illustrates an example process 400 for estimating pupil location from captured image information that can be used in accordance with various embodiments. It should be understood that, for any process discussed herein, there can be additional, fewer, or alternative steps performed in similar or alternative orders, or in parallel, within the scope of the various embodiments unless otherwise stated. In this example, pupil detection is activated 402 on a computing device. As discussed elsewhere herein, this can involve manual activation by a user or automatic activation in response to an action such as the opening of an application or a detection of motion near the device. At least one image can be captured 404 by a camera or other imaging element of a computing device, and at least a portion of that image can be analyzed 406 by a set of pupil location algorithms. The portion to be analyzed can be determined using a pattern or feature recognition algorithm or other such process. Further, the set of algorithms can be preconfigured or selected based at least in part upon information in the image or about the computing device. A set of estimated position values and confidence levels can be obtained 408 from the set of algorithms, and can attempt to determine 410 a probable location of at least one pupil in the image information by analyzing the estimated location and confidence values from each algorithm. As mentioned, each algorithm might produce multiple estimates, each with a different confidence value, and in some embodiments estimates without at least a minimum confidence level can be excluded from the analysis. Various other approaches can be used as well within the scope of the various embodiments.

Additional factors can influence the accuracy of these determinations, however. For example, a situation might arise where two algorithms give a very similar position determination with low confidence values, and other algorithm gives a very different position determination with a high confidence value. In some embodiments, the two similar results might be weighted more highly. If, however, the two algorithms are the same type of algorithm, such as shape-locating algorithms, then less weight might be given as the algorithms might determine the same incorrect location based on current environmental conditions that affect both algorithms in similar ways.

In some embodiments, a pupil detection routine might select algorithms to use to analyze an image based at least in part upon one or more environmental conditions determined for the time of image capture. For example, if the device detects that there is a lot of light near the device, such as through an initial analysis of the image or from information provided by a light sensor, the pupil detection routine might select algorithms that provide relatively accurate results even in the presence of high intensity light. Similarly, if the device can perform an initial analysis on the image, or execute another such process, to determine that the user is not facing the camera in the image, the routine might select algorithms that work better for different relative orientations of the user. Similar approaches can be used for other conditions as well, such as algorithms that work better close up versus far away, during periods of motion versus stable images, etc.

In at least some embodiments, a pupil detection routine might instead utilize a selection of three algorithms that each produce different levels of confidence for different environmental conditions. For example, a device might utilize a shape-based algorithm, a retro-reflection based algorithm, and a glint-based algorithm. Since each algorithm relies upon a substantially different type of information, the algorithms can be less likely to produce similar incorrect results due to a current environmental condition.

Figure 5:
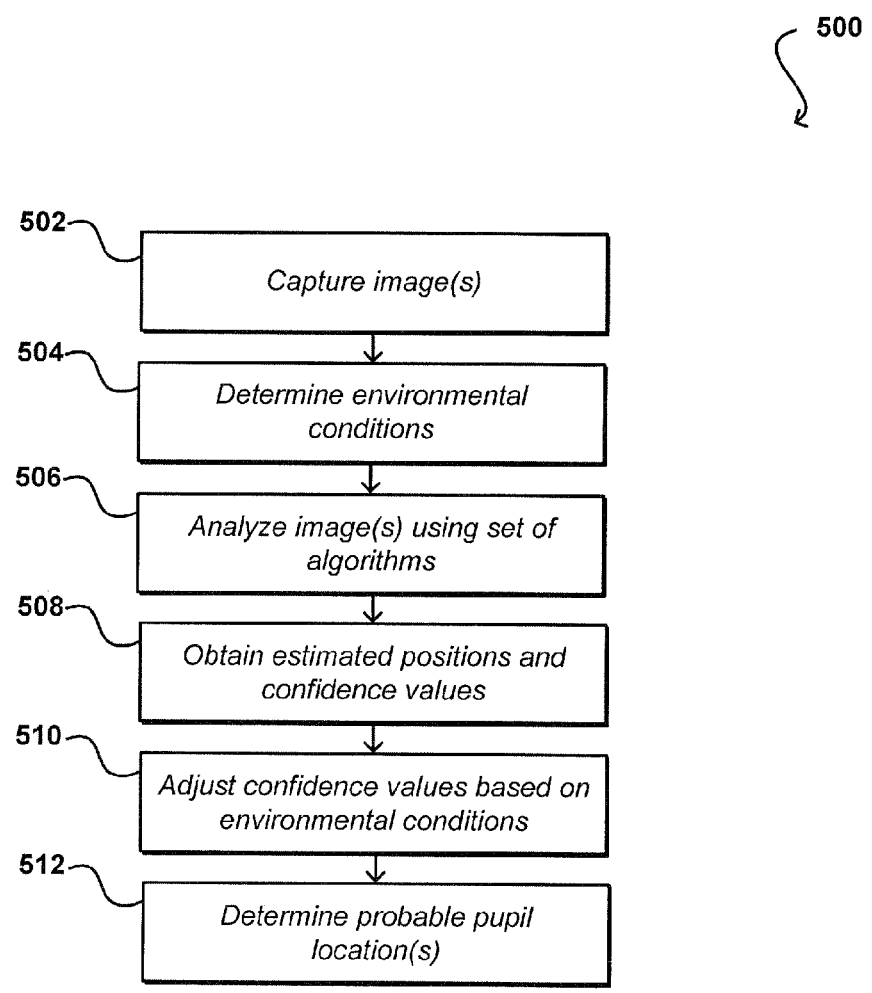
FIG. 5 illustrates an example process for determining pupil location using environmental information in accordance with various embodiments.

FIG. 5 illustrates an example process 500 for determining pupil location that can be used in accordance with various embodiments. In this example, one or more images are captured 502 using a camera of a computing device. Near the time of image capture, one or more environmental conditions can be determined 504. As discussed, this can involve factors such as an amount of ambient light, a relative orientation of the user, an amount of movement of the device, or other such factors. At least a portion of the captured image can be analyzed 506 by a set of pupil location algorithms. In at least some embodiments, the set of algorithms might be selected based at least in part upon any determined environmental condition. A set of estimated position values and confidence levels is obtained 508 from the set of algorithms. Based at least in part upon the determined environmental conditions, the confidence values for at least one algorithm can be adjusted 510, or those values weighted, in order to account for performance of that algorithm under those environmental conditions. Using the weightings or updated confidence levels for the location estimates, at least one algorithm can be used to attempt to determine 512 a most probable location of at least one pupil in the image information. This information can then be used for various purposes discussed herein, such as to assist with gaze direction or point of view determinations. Various other approaches can be used as well within the scope of the various embodiments.

In some embodiments, an approach might categorize shape-based algorithms together, as well as other similar types of algorithms, based on one or more shared aspects of those algorithms. As should be recognized, however, algorithms that are looking for pairs of triangles will likely produce different confidence levels for a given image under certain conditions than an algorithm looking for concentric circles or ellipses of certain size ratios. Under certain circumstance, a circle-based algorithm might instead act more like a retro-reflection algorithm than a triangle pair-based algorithm.

Accordingly, approaches in accordance with various embodiments attempt to determine an "independence" or other such measure between the various algorithms. For example, a Hough circle finding algorithm might have a very weak independence from a starburst algorithm, since both algorithms rely on locating circle-based shapes. On the other hand, a bright pupil finding algorithm might have a very high level of independence from an algorithm that tracks object position between subsequent frames of image information. The bright pupil finding algorithm might have a relatively high level of independence from the circle-based algorithms. In at least some embodiments, a process can attempt to determine a measure of independence between various algorithms. The measure of independence can be used to improve the accuracy of the position determinations, as the location can be based on a calculation such as a probability based on the estimated confidence for each result from a given algorithm, as weighted by their relative independence. In some embodiments, a Bayesian statistic or similar value can be computed based at least in part upon the estimated locations from different algorithms weighted by the determined independence between those algorithms and the respective confidence values.

In one example, a first algorithm and a second algorithm might produce estimates with lower confidence values than a third algorithm with a higher confidence value. The third algorithm, however, might have a relatively low independence score with the first algorithm. Algorithms in accordance with various embodiments might rely more heavily on the value produced by the second algorithm that is significantly independent from the first and third algorithms, as two algorithms with low independence values that produce very different results can be determined to be unreliable for the analyzed image (since low independence algorithms should produce substantially similar results). Similarly, if two algorithms are not significantly independent and have low confidence values, approaches in accordance with various embodiments might ignore the results from both algorithms, or at least weight those values significantly less.

One approach to determining the independence scores or levels between various algorithms involves obtaining a set of images of users having different eye types and looking in different directions under various environmental conditions, for example, and analyzing each of those images with the various algorithms. For each image, a known "correct" result can be determined. The results of each algorithm for that image can then be compared, to determine which algorithms generated substantially similar results. In particular, an analysis can be done to determine how often any two of the algorithms came up with substantially the same incorrect answer. Such an approach can provide an indication of how likely the algorithms are to produce similar results for an image. In addition, such an approach can also provide an indication of how likely the algorithms are to produce similar results for a particular environmental condition or type of information. For example, two algorithms might be substantially independent under different lighting conditions, but very lowly independent upon variations in user orientation, such that a single independence score might be insufficient for at least some situations. In many cases, algorithms producing the same correct answer can provide very little information as to the relative independence of those algorithms. Each pair of algorithms can have at least some level of dependence or independence, as each pair of algorithms will sometimes produce different results for various images.

As discussed, a degree or amount of dependence between two algorithms can provide a measure of how confident a process can be in the results produced by those algorithms. In at least some embodiments, a joint probability distribution can be calculated across the various algorithms. When a new image is obtained, if information such as the eye type and environmental conditions can be determined, a set of algorithms can be selected that will most likely produce accurate results. In other embodiments, the distribution can be used to apply weighting values to the results from the various algorithms used on a device. Various other approaches can be utilized as well within the scope of the various embodiments.

Figure 6:
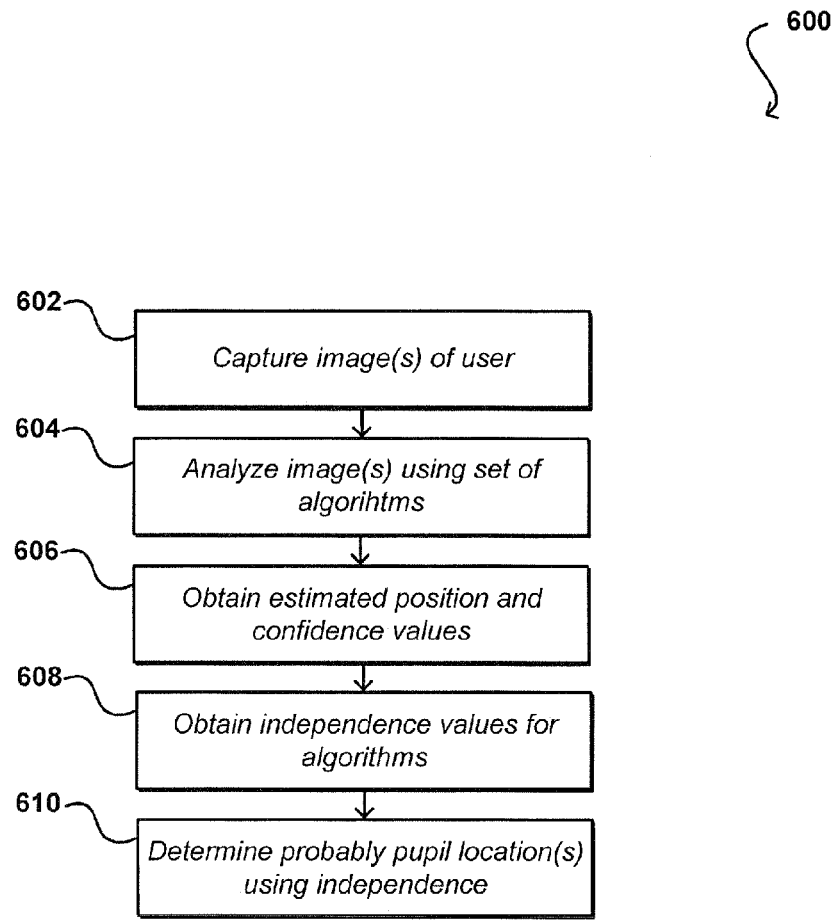
FIG. 6 illustrates an example process for determining pupil location using dependence values among various algorithms in accordance with various embodiments.

FIG. 6 illustrates an example process 600 for determining pupil location that can be used in accordance with various embodiments. In this example, one or more images are captured 602 using a camera of a computing device. At least a portion of the captured image then is analyzed 604 using a set of pupil location algorithms. A set of estimated position values and confidence levels is obtained 606 from the set of algorithms. A set or distribution of independence values for the set algorithms is also obtained 608, which can provide information about the relative dependence between algorithms of the set as discussed herein, and in at least some embodiments is obtained before image capture and/or analysis. The independence information can be used with the estimated position and confidence values to determine 610 a most probable location of at least one pupil in the image information. Various statistical analysis and other such approaches can be used to apply the independence values as discussed and suggested elsewhere herein.

Another approach that can be used in accordance with various embodiments captures at least two images of the user at substantially the same time, such as by using stereo cameras useful for capturing 3D images. In such an embodiment, the set of algorithms for a device can be run on both images. Using approaches known in the art for stereo-imaging, an algorithm can determine the amount of offset in each image due to the placement and/or separation of the cameras. Using this information, an algorithm can correlate positions in the two images, such that a position in space can be matched with a position in each of the images. The estimates of each algorithm then also can be compared for each image to determine whether each algorithm produced estimates that substantially match for each image. If, for example, the results of a Hough circle finder algorithm produce an estimated position for the first image that is substantially different from the estimated position of the second image, then those estimates can be given a lower weighting or even ignored. If the estimates match for each image this still may not result in an increased weighting, however, as the algorithm might identify an inaccurate position based on the same feature or environmental condition present in both images. In some embodiments, each algorithm can analyze the images together and determine how well the estimates for each image match based on the known geometry of the cameras, and can adjust or set the confidence values accordingly.

In some embodiments, it can be desirable to minimize the use of resources, such as processing and power consumption, by preventing unnecessary execution of multiple algorithms on captured images, which can be very processor intensive in at least some embodiments. In at least one embodiment, a device can utilize an approach to determine whether a feature in a field of view of a camera corresponds to a human eye before attempting to perform pupil location with a set of algorithms. For example, a shape-based pupil detector can provide a likelihood that a feature exhibits saline-like features. In other embodiments, a dual-wavelength approach can be used to detect whether a feature is likely a human eye. For example, a device might detect motion near the device, such as by using a motion detector or low resolution camera, etc. In response, the device can emit infrared radiation at two different wavelengths and capture image information using at least one IR sensor or camera that is able to capture information at those wavelengths. Since the human eye absorbs one of those wavelengths and reflects the other, a difference in reflected IR can be indicative of the response of a human eye. More detail for potential dual-wavelength approaches can be found, for example, in co-pending U.S. patent application Ser. No. 12/786,297, filed May 24, 2010, and entitled "Determining Relative Motion as Input," which is hereby incorporated herein by reference. Once it is determined that a human eye is present in the field of view of the camera, or at least in a range of detectable positions with respect to the device, the device in some embodiments can begin the pupil detection analysis. Other approaches such as facial recognition can be used as well, but such approaches can potentially be susceptible to false positives for images of human faces, and further are themselves typically very processor intensive.

Another approach that can potentially save resources involves maintaining information about eye type for a user. As mentioned above, algorithms work differently with eyes of different shape, size, and color, among other such aspects. In at least some embodiments, an initial determination of the type of eye of a user can be performed, such as through image analysis and feature recognition, for example, when the user initially utilizes a process that requires pupil location, eye detection, or another such process. This information can include a type and/or information such as dimensions, shape, color, etc. This information can be stored by the device, or at least accessible to the device, such that when that user is subsequently recognized to the device (i.e., through facial recognition, biometric identification, password entry, or another such mechanism) the device can load or retrieve the eye information for that user without having to make another determination.

The eye information stored for a user can also be updated over time. For example, a device can be configured to periodically re-examine image information for a user to ensure any changes in eye information are updated in the stored information. In some embodiments, a device might detect different user states, such as when a user is wearing glass or not wearing glasses, and can store eye information for each state. A determination that the user is wearing glasses then can be used to load the proper eye information to use in weighting results from various algorithms, selecting algorithms to use, etc. Certain embodiments can utilize information from the pupil determination algorithms to continually update eye information. In some embodiments, there might be a weighted combination of information to produce the stored eye information, such that information from multiple determinations can be combined to generate a more accurate picture of the user's eye, and these values can be weighted or decayed such that more recent determinations can affect the eye information more than previous determinations. In some embodiments, the accuracy or confidence levels of various algorithms can be monitored, and a detected decrease in overall accuracy or confidence might cause a redetermination of eye type and/or parameters to be determined.

Figure 7:
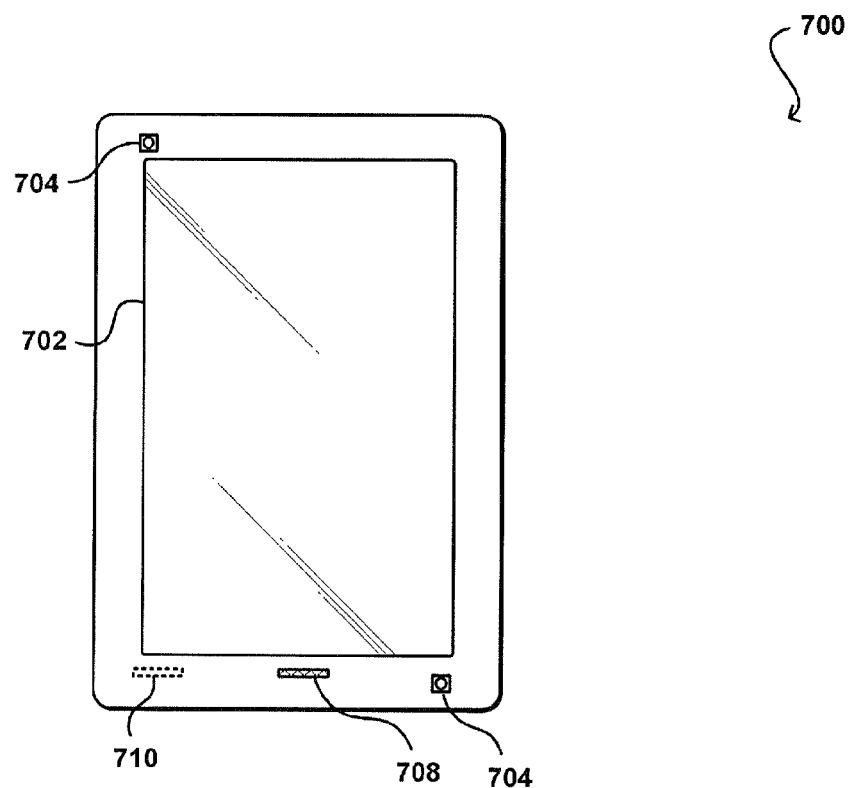
FIG. 7 illustrates an example computing device including elements operable to capture gaze information that can be used in accordance with various embodiments.

FIG. 7 illustrates an example of a computing device 700 that can be used in accordance with various embodiments. Although a portable computing device (e.g., a smart phone, an electronic book reader, or tablet computer) is shown, it should be understood that any device capable of receiving and processing input can be used in accordance with various embodiments discussed herein. The devices can include, for example, desktop computers, notebook computers, electronic book readers, personal data assistants, cellular phones, video gaming consoles or controllers, television set top boxes, and portable media players, among others.

In this example, the computing device 700 has a display screen 702, which under normal operation will display information to a user facing the display screen (e.g., on the same side of the computing device as the display screen). The computing device in this example can include one or more image capture elements, in this example including two image capture elements 704 on the front side of the device, although it should be understood that image capture elements could also, or alternatively, be placed on the sides or corners of the device, and that there can be any appropriate number of capture elements of similar or different types. Each image capture element 704 may be, for example, a camera, a charge-coupled device (CCD), a motion detection sensor, or an infrared sensor, or can utilize any other appropriate image capturing technology. The computing device can also include at least one microphone 708 or other audio capture element(s) capable of capturing other types of input data. At least one orientation-determining element 710 can be used to detect changes in position and/or orientation of the device. Various other types of input can be utilized as well as known in the art for use with such devices.

Figure 8:
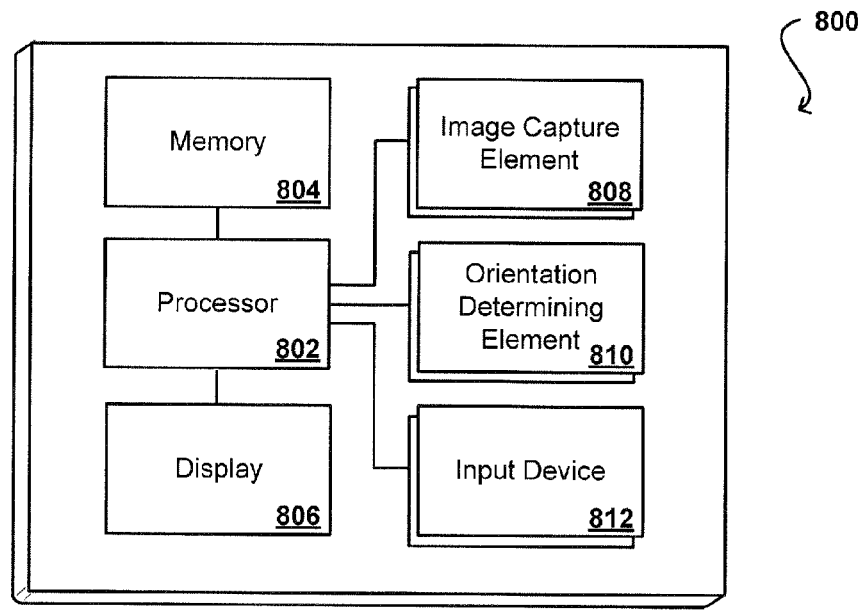
FIG. 8 illustrates example components of a computing device such as that illustrated in FIG. 7.

FIG. 8 illustrates a set of basic components of a computing device 800 such as the device 700 described with respect to FIG. 7. In this example, the device includes at least one processor 802 for executing instructions that can be stored in a memory device or element 804. As would be apparent to one of ordinary skill in the art, the device can include many types of memory, data storage or computer-readable media, such as a first data storage for program instructions for execution by the processor 802, the same or separate storage can be used for images or data, a removable memory can be available for sharing information with other devices, and any number of communication approaches can be available for sharing with other devices. The device typically will include some type of display element 806, such as a touch screen, electronic ink (e-ink), organic light emitting diode (OLED) or liquid crystal display (LCD), although devices such as portable media players might convey information via other means, such as through audio speakers. As discussed, the device in many embodiments will include at least one image capture element 808 able to image a user, people, or objects in the vicinity of the device. An image capture element can include any appropriate technology, such as a CCD image capture element having a sufficient resolution, focal range and viewable area, to capture an image of the user when the user is operating the device. Methods for capturing images or video using an image capture element with a computing device are well known in the art and will not be discussed herein in detail. It should be understood that image capture can be performed using a single image, multiple images, periodic imaging, continuous image capturing, image streaming, etc.

Further, a device can include the ability to start and/or stop image capture, such as when receiving a command from a user or an application, or retrying to determine an audio input or other device. In some embodiments, a device can include an infrared detector or motion sensor, for example, which can be used to activate an imaging element, image analysis, etc. For example, a device might not capture and analyze image information when there is not a user in the room. If an infrared detector (i.e., a detector with one-pixel resolution that detects changes in state) detects a user entering the room, for example, the device can activate a camera in an attempt to locate the user, perform image analysis, etc.

The device can include at least one additional input device 812 able to receive conventional input from a user. This conventional input can include, for example, a push button, touch pad, touch screen, wheel, joystick, keyboard, mouse, trackball, keypad or any other such device or element whereby a user can input a command to the device. These I/O devices could even be connected by a wireless infrared or Bluetooth or other link as well in some embodiments. In some embodiments, however, such a device might not include any buttons at all and might be controlled only through a combination of visual and audio commands such that a user can control the device without having to be in contact with the device.

In at least some embodiments, a device can utilize at least one image capture element and/or audio capture element to attempt to recognize or authenticate the identity of a particular user. In one example, there might be several people sitting around a table on which the device has been placed, and these people might shift positions over time. If the device is able to capture images of these people, or capture voice data, etc., the device can attempt to identify at least the primary user of the device, if not others around the device. In some embodiments the device can use image or voice recognition, while in other embodiments heat signatures or other appropriate types of info niation can be used. Being able to determine the identity of the primary user can help to ensure that only the appropriate user is able to provide input to the device, and that input is not inadvertently processed for other persons who might also be glancing at the device. In some embodiments, the ability to tell that a person who is not an authorized user is glancing at the device can cause the device to perform other actions, such as to turn off a display or only show certain types of information, in order to prevent unauthorized users from viewing private or sensitive information on the device. In some embodiments where there can be multiple authorized users, the ability to recognize the identity of a given user can enable the device to display information at a rate or following an access pattern in ways that are customized for that user. For example, if a husband and wife share a device and the wife is gazing at the device, the device can display information at a rate that has been determined for the wife. Various other differences in functionality can be presented based on user identity as well within the scope of the various embodiments.

Figure 9A:
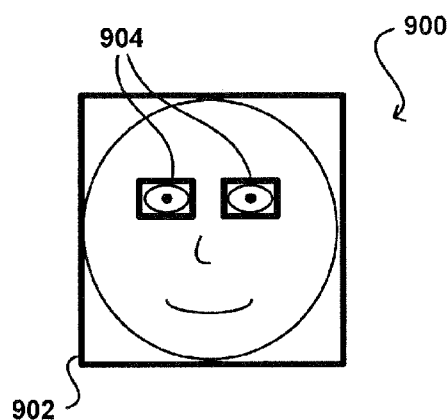
FIGS. 9(a)-9(f) illustrate example approaches to determining user input that can be used in accordance with various embodiments.

Various approaches can be utilized for locating one or more desired features of a user's face to determine various aspects useful for determining relative orientation. For example, if a user's head is to be used as input, there can be many objects that can be shaped similar to a human head that could give false readings. Also, a user nodding "no" might not actually move the position of the user's head enough to register the movement. Accordingly, various approaches utilize features such as a user's eyes to assist in position and movement determination. For example, an image can be analyzed to determine the approximate location and size of a user's head or face. FIG. 9(a) illustrates an example wherein the approximate position and area of a user's head or face 900 is determined and a virtual "box" 902 is placed around the face as an indication of position using one of a plurality of image analysis algorithms for making such a determination. Using one algorithm, a virtual "box" is placed around a user's face and the position and/or size of this box is continually updated and monitored in order to monitor relative user position. Similar algorithms can also be used to determine an approximate location and area 904 of each of the user's eyes (or in some cases the eyes in tandem). By determining the location of the user's eyes as well, advantages can be obtained as it can be more likely that the image determined to be the user's head actually includes the user's head, and it can be determined that the user is facing the device. Further, the relative movement of the user's eyes can be easier to detect than the overall movement of the user's head when performing motions such as nodding or shaking the head back and forth.

Figure 9B:
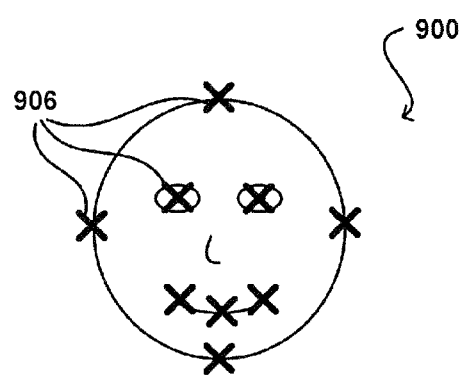

Various other algorithms can be used to determine the location of features on a user's face. For example, FIG. 9(b) illustrates an example wherein various features on a user's face are identified and assigned a point location 906 in the image. The system thus can detect various aspects of user features and can determine changes such as movement or change in shape or expression. Such an approach provides advantages over the general approach of FIG. 9(a) in certain situations, as various points along a feature can be determined, such as the end points and at least one center point of a user's mouth. Accordingly, expressions such as a smile or frown can be captured even though the overall position of the user's mouth or face did not move.

Figure 9C:
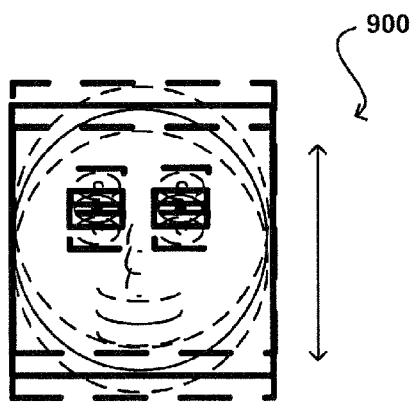
Figure 9D:
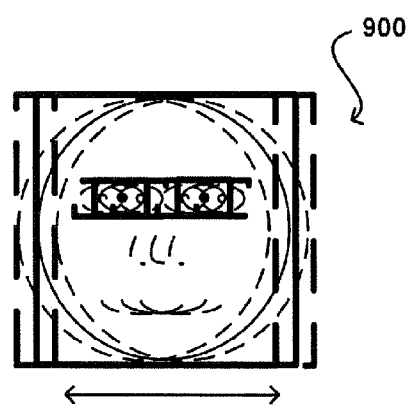
Figure 9E:
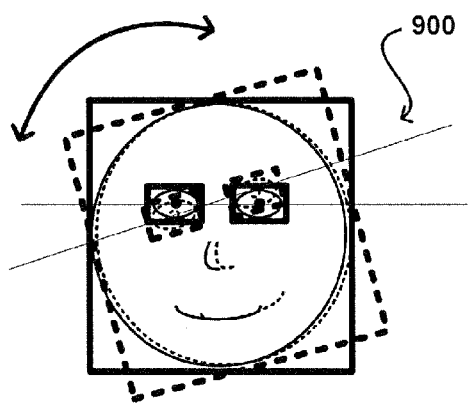

Once the positions of facial features of a user are identified, relative motion between the user and the device can be detected and utilized as input. For example, FIG. 9(c) illustrates an example where the user's head 900 is moving up and down with respect to the viewable area of the imaging element. As discussed, this could be the result of the user shaking his or her head, or the user moving the device up and down, etc. FIG. 9(d) illustrates a similar example wherein the user is moving right to left relative to the device, through movement of the user, the device, or both. As can be seen, each movement can be tracked as a vertical or horizontal movement, respectively, and each can be treated differently as an input to perform a specified function. In one example, the monitored movements are used to control the position of a cursor on the interface display by following the up, down, and across motions. As should be understood, such a process also can detect diagonal or other such movements. FIG. 9(e) further illustrates an example wherein the user tilts the device and/or the user's head, and the relative change in eye position is detected as a rotation. In some systems, a "line" that corresponds to the relative position of the eyes can be monitored, and a shift in angle of this line can be compared to an angle threshold to determine when the rotation should be interpreted as input.

Figure 9F:
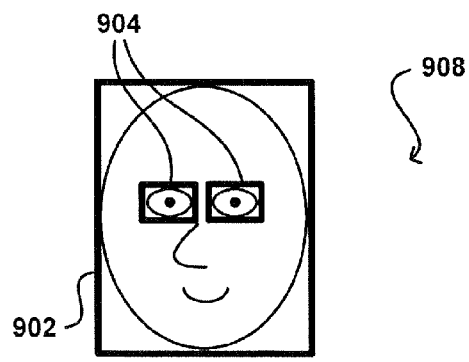

FIG. 9(f) illustrates another advantage of using an approach such as that described with respect to FIG. 9(b) to determine the position of various features on a user's face. In this exaggerated example, it can be seen that the features of a second user's head 908 have a different relative position and separation. Thus, the device also can not only determine positions of features for a user, but can distinguish between different users. As discussed later herein, this can allow the device to perform differently for inputs from different users. Also, the device can be configured to detect how close a user is to the device based on, for example, the amount and ratio of separation of various features, such that the device can detect movement towards, and away from, the device. This can help to improve the accuracy of gaze detection.

Figure 10A:
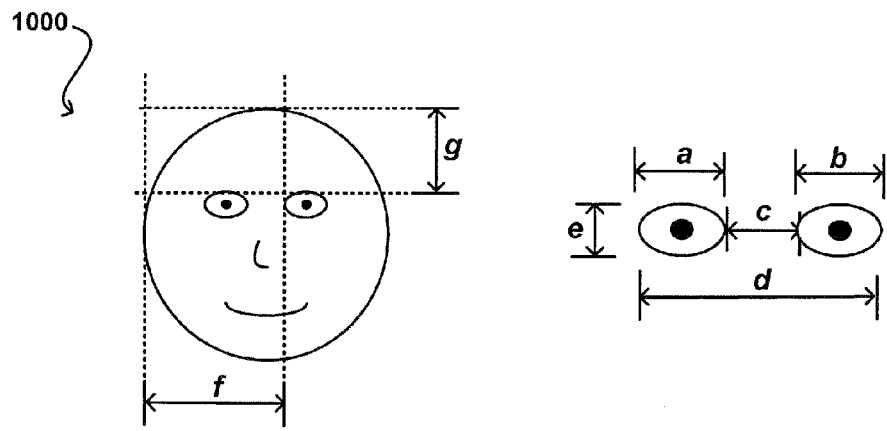
FIGS. 10(a)-10(c) illustrate example approaches to determining glance direction that can be used in accordance with various embodiments.
Figure 10B:
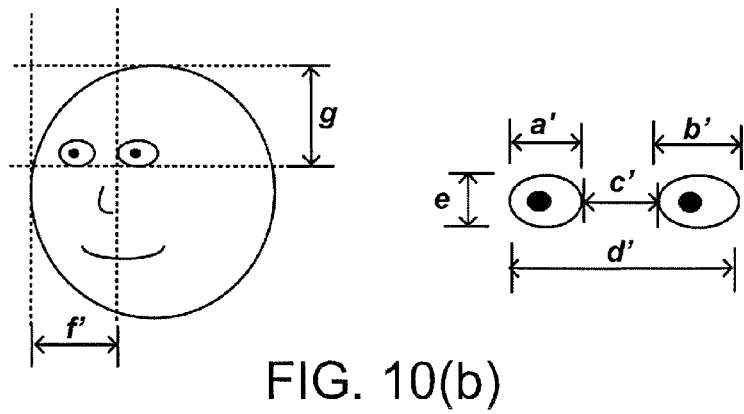
Figure 10C:
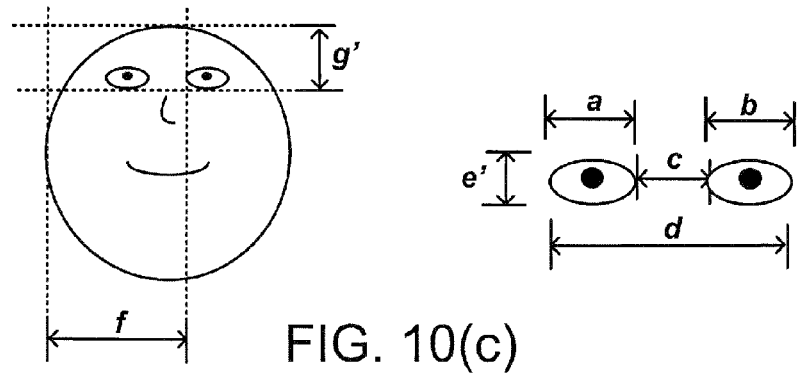

In order to determine the gaze direction of a user for such a process, the device in at least some embodiments has to determine the relative position of the user relative to the device, as well as dimensions or other aspects of the user at that position. FIG. 10(a) illustrates an example 1000 wherein images are captured and analyzed to determine the relative positions of the user's head and the user's eyes. In a system wherein the algorithm is able to differentiate the user's pupils, the system can also utilize the relative position of the pupils with respect to the eye position. For example, FIG. 10(b) illustrates a case where the user is looking "left" (or to the user's right"), such that a center point of each user's pupil is to the left (in the image) of the center point of the respective eye. Similarly, FIG. 10(c) illustrates a case where the user is looking "up". As can be seen, the positions of the pupils have moved above a center point of the eyes. The position of the pupils can change without the user moving his or her head. Thus the system may be able to, in some embodiments, detect a glance without a change in head position. A system in accordance with one embodiment can take advantage of such information by adjusting the display of the computing device according to the detected position of the user's pupils relative to the user's eyes, and thus the determined area on the display at which the user is looking. A system can also detect movements such as a user closing his or her eyes for an extended period of time, wherein the device can perform an action such as placing an electronic book reader in a "sleep" or power-limiting mode, deactivating image capture, or powering off the device. A system in some embodiments can differentiate between different types of movement, such as between eye tremor, smooth tracking, and ballistic movements. In some embodiments, a user can provide specific input though various eye gestures, such as for a glance or gaze associated with a specific ballistic movement. A system could also require no ballistic movement in a continued gaze for certain input or actions, such as to enable a user to obtain additional information of the current type.

In some embodiments, a computing device can determine and track an approximate area or region of interest corresponding to the user's eyes, or another such feature, in the captured images such that an algorithm of the computing device only has to analyze image data corresponding to that region, which can significantly reduce the amount of processing needed for images, particularly for high resolution, full color images.

A number of other approaches can be used as well within the scope of the various embodiments. For example, thermal imaging or another such approach could be used to attempt to determine and track the position of at least some aspect of a human user. In many instances the imaging system is desired to be small and inexpensive enough for mass marketing, such that simple or conventional imaging approaches and components can be preferred. Certain existing cameras can detect infrared radiation, but typically utilize an IR filter. Utilizing these relatively inexpensive cameras without the IR filter, and potentially with an ambient light filter, can allow the cameras to be used as IR detectors.

Figure 11:
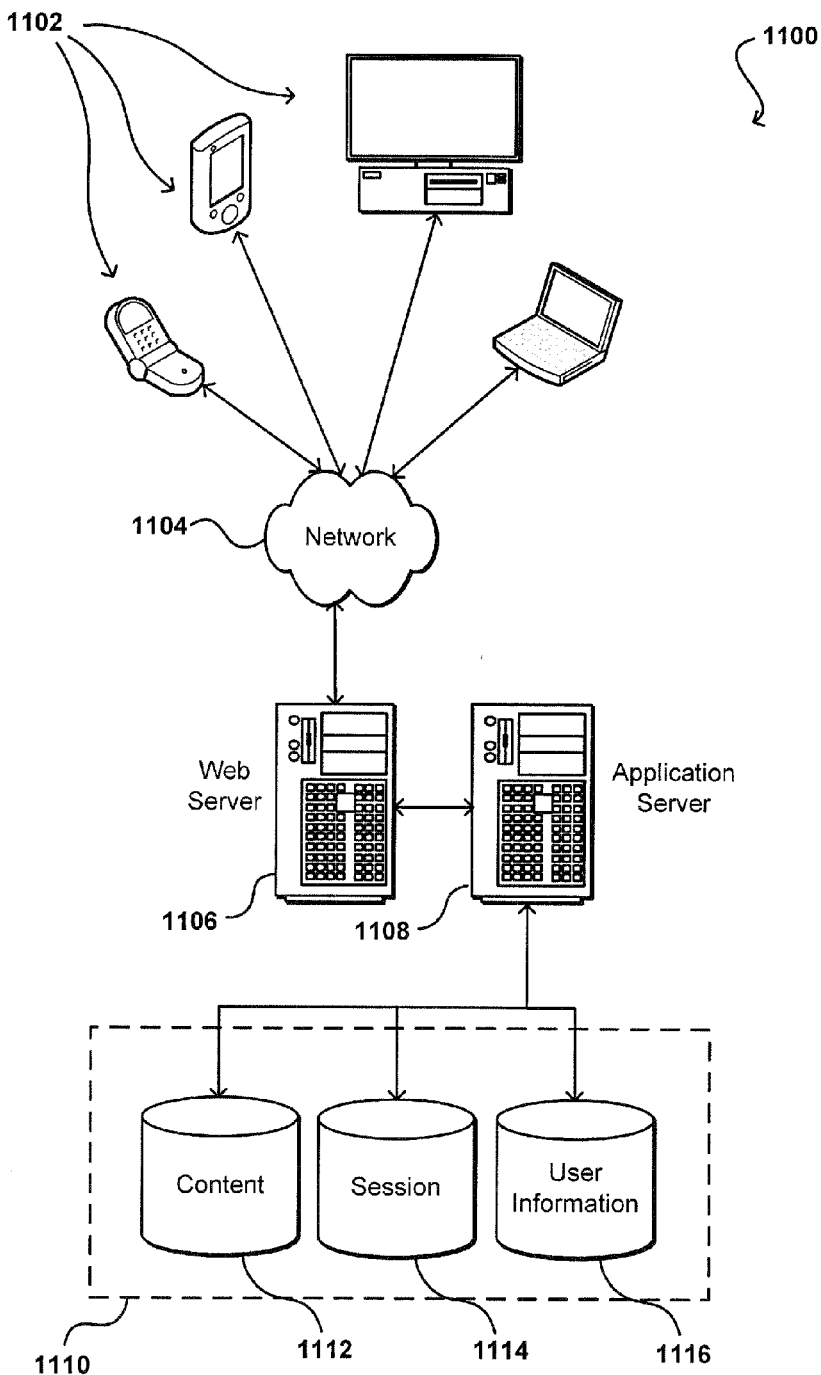
FIG. 11 illustrates an environment in which various embodiments can be implemented.

As discussed, different approaches can be implemented in various environments in accordance with the described embodiments. For example, FIG. 11 illustrates an example of an environment 1100 for implementing aspects in accordance with various embodiments. As will be appreciated, although a Web-based environment is used for purposes of explanation, different environments may be used, as appropriate, to implement various embodiments. The system includes an electronic client device 1102, which can include any appropriate device operable to send and receive requests, messages or information over an appropriate network 1104 and convey information back to a user of the device. Examples of such client devices include personal computers, cell phones, handheld messaging devices, laptop computers, set-top boxes, personal data assistants, electronic book readers and the like. The network can include any appropriate network, including an intranet, the Internet, a cellular network, a local area network or any other such network or combination thereof. Components used for such a system can depend at least in part upon the type of network and/or environment selected. Protocols and components for communicating via such a network are well known and will not be discussed herein in detail. Communication over the network can be enabled via wired or wireless connections and combinations thereof. In this example, the network includes the Internet, as the environment includes a Web server 1106 for receiving requests and serving content in response thereto, although for other networks, an alternative device serving a similar purpose could be used, as would be apparent to one of ordinary skill in the art.

The illustrative environment includes at least one application server 1108 and a data store 1110. It should be understood that there can be several application servers, layers or other elements, processes or components, which may be chained or otherwise configured, which can interact to perform tasks such as obtaining data from an appropriate data store. As used herein, the term "data store" refers to any device or combination of devices capable of storing, accessing and retrieving data, which may include any combination and number of data servers, databases, data storage devices and data storage media, in any standard, distributed or clustered environment. The application server 1108 can include any appropriate hardware and software for integrating with the data store 1110 as needed to execute aspects of one or more applications for the client device and handling a majority of the data access and business logic for an application. The application server provides access control services in cooperation with the data store and is able to generate content such as text, graphics, audio and/or video to be transferred to the user, which may be served to the user by the Web server 1106 in the form of HTML, XML or another appropriate structured language in this example. The handling of all requests and responses, as well as the delivery of content between the client device 1102 and the application server 1108, can be handled by the Web server 1106. It should be understood that the Web and application servers are not required and are merely example components, as structured code discussed herein can be executed on any appropriate device or host machine as discussed elsewhere herein.

The data store 1110 can include several separate data tables, databases or other data storage mechanisms and media for storing data relating to a particular aspect. For example, the data store illustrated includes mechanisms for storing content (e.g., production data) 1112 and user information 1116, which can be used to serve content for the production side. The data store is also shown to include a mechanism for storing log or session data 1114. It should be understood that there can be many other aspects that may need to be stored in the data store, such as page image information and access rights information, which can be stored in any of the above listed mechanisms as appropriate or in additional mechanisms in the data store 1110. The data store 1110 is operable, through logic associated therewith, to receive instructions from the application server 1108 and obtain, update or otherwise process data in response thereto. In one example, a user might submit a search request for a certain type of item. In this case, the data store might access the user information to verify the identity of the user and can access the catalog detail information to obtain information about items of that type. The information can then be returned to the user, such as in a results listing on a Web page that the user is able to view via a browser on the user device 1102. Information for a particular item of interest can be viewed in a dedicated page or window of the browser.

Each server typically will include an operating system that provides executable program instructions for the general administration and operation of that server and typically will include computer-readable medium storing instructions that, when executed by a processor of the server, allow the server to perform its intended functions. Suitable implementations for the operating system and general functionality of the servers are known or commercially available and are readily implemented by persons having ordinary skill in the art, particularly in light of the disclosure herein.

The environment in one embodiment is a distributed computing environment utilizing several computer systems and components that are interconnected via communication links, using one or more computer networks or direct connections. However, it will be appreciated by those of ordinary skill in the art that such a system could operate equally well in a system having fewer or a greater number of components than are illustrated in FIG. 11. Thus, the depiction of the system 1100 in FIG. 11 should be taken as being illustrative in nature and not limiting to the scope of the disclosure.

The various embodiments can be further implemented in a wide variety of operating environments, which in some cases can include one or more user computers or computing devices which can be used to operate any of a number of applications. User or client devices can include any of a number of general purpose personal computers, such as desktop or laptop computers running a standard operating system, as well as cellular, wireless and handheld devices running mobile software and capable of supporting a number of networking and messaging protocols. Such a system can also include a number of workstations running any of a variety of commercially-available operating systems and other known applications for purposes such as development and database management. These devices can also include other electronic devices, such as dummy terminals, thin-clients, gaming systems and other devices capable of communicating via a network.

Most embodiments utilize at least one network that would be familiar to those skilled in the art for supporting communications using any of a variety of commercially-available protocols, such as TCP/IP, OSI, FTP, UPnP, NFS, CIFS and AppleTalk. The network can be, for example, a local area network, a wide-area network, a virtual private network, the Internet, an intranet, an extranet, a public switched telephone network, an infrared network, a wireless network and any combination thereof.

In embodiments utilizing a Web server, the Web server can run any of a variety of server or mid-tier applications, including HTTP servers, FTP servers, CGI servers, data servers, Java servers and business application servers. The server(s) may also be capable of executing programs or scripts in response requests from user devices, such as by executing one or more Web applications that may be implemented as one or more scripts or programs written in any programming language, such as Java®, C, C# or C++ or any scripting language, such as Perl, Python or TCL, as well as combinations thereof. The server(s) may also include database servers, including without limitation those commercially available from Oracle®, Microsoft®, Sybase® and IBM®.

The environment can include a variety of data stores and other memory and storage media as discussed above. These can reside in a variety of locations, such as on a storage medium local to (and/or resident in) one or more of the computers or remote from any or all of the computers across the network. In a particular set of embodiments, the information may reside in a storage-area network (SAN) familiar to those skilled in the art. Similarly, any necessary files for performing the functions attributed to the computers, servers or other network devices may be stored locally and/or remotely, as appropriate. Where a system includes computerized devices, each such device can include hardware elements that may be electrically coupled via a bus, the elements including, for example, at least one central processing unit (CPU), at least one input device (e.g., a mouse, keyboard, controller, touch-sensitive display element or keypad) and at least one output device (e.g., a display device, printer or speaker). Such a system may also include one or more storage devices, such as disk drives, optical storage devices and solid-state storage devices such as random access memory (RAM) or read-only memory (ROM), as well as removable media devices, memory cards, flash cards, etc.

Such devices can also include a computer-readable storage media reader, a communications device (e.g., a modem, a network card (wireless or wired), an infrared communication device) and working memory as described above. The computer-readable storage media reader can be connected with, or configured to receive, a computer-readable storage medium representing remote, local, fixed and/or removable storage devices as well as storage media for temporarily and/or more permanently containing, storing, transmitting and retrieving computer-readable information. The system and various devices also typically will include a number of software applications, modules, services or other elements located within at least one working memory device, including an operating system and application programs such as a client application or Web browser. It should be appreciated that alternate embodiments may have numerous variations from that described above. For example, customized hardware might also be used and/or particular elements might be implemented in hardware, software (including portable software, such as applets) or both. Further, connection to other computing devices such as network input/output devices may be employed.

Storage media and computer readable media for containing code, or portions of code, can include any appropriate media known or used in the art, including storage media and communication media, such as but not limited to volatile and non-volatile, removable and non-removable media implemented in any method or technology for storage and/or transmission of information such as computer readable instructions, data structures, program modules or other data, including RAM, ROM, EEPROM, flash memory or other memory technology, CD-ROM, digital versatile disk (DVD) or other optical storage, magnetic cassettes, magnetic tape, magnetic disk storage or other magnetic storage devices or any other medium which can be used to store the desired information and which can be accessed by a system device. Based on the disclosure and teachings provided herein, a person of ordinary skill in the art will appreciate other ways and/or methods to implement the various embodiments.

The specification and drawings are, accordingly, to be regarded in an illustrative rather than a restrictive sense. It will, however, be evident that various modifications and changes may be made thereunto without departing from the broader spirit and scope of the invention as set forth in the claims.

What is claimed is:

1. A method of determining pupil location, comprising:
    capturing an image using a camera of a computing device, the image including at least a portion of a user positioned at least partially within a field of view of the camera;
    determining at least one environmental condition at approximately a time the image is captured;
    determining a first estimated pupil location using a first pupil location determination algorithm, the first pupil location determination algorithm returning a first confidence value corresponding to the first estimated pupil location;
    determining a second estimated pupil location using at least one second pupil location determination algorithm, the at least one second pupil location determination algorithm returning at least one second confidence value corresponding to the at least one second estimated pupil location, the first pupil location determination algorithm being different from the at least one second pupil location determination algorithm;
    adjusting using a processor of the computing device, the first confidence value based at least in part upon performance of the first pupil location determination algorithm associated with the at least one environmental condition;
    adjusting, using the processor of the computing device, the at least one second confidence value based at least in part upon performance of the at least one second pupil location determination algorithm associated with the at least one environmental condition; and
    determining a pupil location for an eye of the user with respect to the computing device based at least in part on a combination of the first estimated pupil location and the at least one second estimated pupil location weighted by the adjusted first confidence value and the adjusted at least one second confidence value.

2. The method of claim 1, wherein the at least one environmental condition corresponds to an amount of light, a relative orientation of the user, or an amount of motion of the computing device.

3. The method of claim 1, further comprising:
    selecting the first pupil location determination algorithm and the at least one second pupil location determination algorithm from a set of pupil location determination algorithms based at least in part upon at least one of the at least one environmental condition or at least one characteristic of the eye of the user.

4. A computer-implemented method of determining relative pupil location for a user with respect to an electronic device, comprising:
    capturing an image using a camera of the electronic device, the image including at least a portion of a user positioned at least partially within a field of view of the camera;
    determining a first estimated pupil location using a first pupil location determination algorithm, the first pupil determination algorithm returning a first confidence value corresponding to the first estimated pupil location;
    determining a second estimated pupil location using at least one second pupil location determination algorithm, the at least one second pupil location determination algorithm returning at least one second confidence value corresponding to the at least one second estimated pupil location, the first pupil location determination algorithm being different from the at least one second pupil location determination algorithm; and determining a pupil location for an eye of the user with respect to the electronic device based at least in part on a combination of the first estimated pupil location and the at least one second estimated pupil location weighted by the first confidence value and the at least one second confidence value.

5. The computer-implemented method of claim 4, wherein the first estimated pupil location and the second estimated pupil location corresponds to at least one of a pixel location, a vector, or an estimated set of coordinates.

6. The computer-implemented method of claim 4, wherein at least one of the first pupil location determination algorithm or the at least one second pupil location determination algorithm produces multiple estimated pupil locations with corresponding confidence values for the image.

7. The computer-implemented method of claim 4, wherein determining the pupil location includes:
generating a heat map using the first estimated pupil location and the second estimated pupil location and the first confidence value and the at least one second confidence value; and
selecting a highest point on the heat map as the pupil location.

8. The computer-implemented method of claim 4, further comprising:
determining that the first confidence value corresponding to the first estimated pupil location is below a confidence threshold; and
rejecting the first estimated pupil location.

9. The computer-implemented method of claim 4, further comprising:
detecting at least one human eye before analyzing the image using the first pupil location determination algorithm or the second pupil location determination algorithm.

10. The computer-implemented method of claim 4, wherein a pair of images is captured using a pair of cameras on the electronic device, and where results for each of the images for each of the first pupil location determination algorithm and the second pupil location determination algorithm are compared to adjust the confidence value from each estimated pupil location in response to a determined amount of agreement for the pair of images.

11. The computer-implemented method of claim 4, wherein the first pupil location determination algorithm and the second pupil location determination algorithm includes at least one of a shape-based determination algorithm or a retro-reflection-based algorithm.

12. A method of determining pupil location, comprising:
capturing an image using a camera of a computing device, the image including at least a portion of a user positioned at least partially within a field of view of the camera;
analyzing, using a processor of the computing device, the image using each of a set of pupil location determination algorithms, the pupil location determination algorithms having a plurality of levels of independence each indicating a likelihood of a pair of algorithms producing a similar result under similar circumstances;
determining a first estimated pupil location using a first pupil location determination algorithm of the set of location determination algorithms, the first pupil location determination algorithm returning a first confidence value corresponding to the first estimated pupil location;
determining a second estimated pupil location using at least one second pupil location determination algorithm of the set of location determination algorithms, the at least one second pupil location determination algorithm returning at least one second confidence value corresponding to the at least one second estimated pupil location, the first pupil location determination algorithm being different from the at least one second pupil location determination algorithm;
adjusting, using the processor of the computing device, the first confidence value based at least in part upon a corresponding level of independence with respect to the at least one second pupil location algorithm; and
determining a pupil location for an eye of the user with respect to the computing device based at least in part on a combination of the first estimated pupil location and the at least one second estimated pupil location weighted by the first confidence value and the at least one second confidence value after the adjusting based at least in part upon the corresponding level of independence.

13. The method of claim 12, further comprising:
obtaining a set of calibration images each differing in at least one aspect;
analyzing the calibration images using a plurality of pupil location algorithms;
comparing results from the a plurality of pupil location algorithms to determine a likelihood of each pupil location algorithm producing a result similar to each other pupil location algorithm; and
generating the levels of independence for the plurality of pupil location algorithms based on the determined likelihood.

14. The method of claim 13, wherein the at least one aspect includes at least one of intensity, color, user orientation, eye type, blur, or motion.

15. The method of claim 12, wherein there are multiple levels of independence determined for each pupil location algorithm based at least in part upon different environmental conditions.

16. The method of claim 12, further comprising:
generating a probability distribution for the level of independence between the set of algorithms for use in adjusting the confidence values.

17. A computing device, comprising:
a processor;
a camera; and
a memory device including instructions operable to the executed by the processor to perform a set of actions, enabling the computing device to:
capture an image including at least a portion of a user at least partially within a field of view of the camera;
determine a first estimated pupil location using a first pupil location determination algorithm, the first pupil location determination algorithm returning a first confidence value corresponding to the first estimated pupil location;
determine second estimated pupil location using at least one second pupil location determination algorithm, the at least one second pupil location determination algorithm returning at least one second confidence value corresponding to the at least one second estimated pupil location, the first pupil location determination algorithm being different from the at least one second pupil location determination algorithm; and
determine a pupil location for an eye of the user with respect to the computing device based at least in part on a combination of the first estimated pupil location and the at least one second estimated pupil location weighted by the first confidence value and the at least one second confidence value.

18. The computing device of claim 17, further comprising:
a motion detector operable to cause the camera to capture the image in response to detecting motion near the computing device.

19. The computing device of claim 17, further comprising:
a second camera for capturing a second image of the user, the first confidence value for the first pupil location determination algorithm capable of being updated based at least in part upon an a difference in estimated position of the pupil in the second image.

20. A non-transitory computer-readable storage medium storing instructions for determining relative pupil position, the instructions when executing by a processor of a computing device causing the computing device to:
capture an image using a camera of the computing device, the image including at least a portion of a user positioned at least partially within a field of view of the camera;
determine a first estimated pupil location using a first pupil location determination algorithm, the first pupil location determination algorithm returning a first confidence value corresponding to the first estimated pupil location;
determine a second estimated pupil location using at least one second pupil location determination algorithm, the at least one second pupil location determination algorithm returning at least one second confidence value corresponding to the at least one second estimated pupil location, the first pupil location determination algorithm being different from the at least one second pupil location determination algorithm; and
determine a pupil location for an eye of the user with respect to the computing device based at least in part on a combination of the first estimated pupil location and the at least one second estimated pupil location weighted by the first confidence value and the at least one second confidence value.

21. The non-transitory computer-readable storage medium of claim 20, wherein the first pupil location determination algorithm and the second pupil location determination algorithm includes at least one of a shape-based determination algorithm and a retro-reflection-based algorithm.

22. The non-transitory computer-readable storage medium of claim 20, wherein the instructions when executed further cause the computing device to:
detect a human eye before analyzing the image using the first pupil location determination algorithm and the second pupil location determination algorithm.

23. The non-transitory computer-readable storage medium of claim 20, wherein a pair of images is captured using a pair of cameras on the computing device, and where results for each of the images for each of the first pupil location determination algorithm and the second pupil location determination algorithm are compared to adjust the confidence levels value from each estimated pupil location in response to a determined amount of agreement for the pair of images.

* * * * *